(12) United States Patent
Strehl

(10) Patent No.: US 10,143,407 B2
(45) Date of Patent: Dec. 4, 2018

(54) LANCING DEVICE FOR OBTAINING SAMPLES OF BODY FLUID

(71) Applicant: Gerresheimer Regensburg GmbH, Regensburg (DE)

(72) Inventor: Michael Strehl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 157 days.

(21) Appl. No.: 14/422,564

(22) PCT Filed: Jul. 25, 2013

(86) PCT No.: PCT/EP2013/065737
§ 371 (c)(1),
(2) Date: Jun. 7, 2015

(87) PCT Pub. No.: WO2014/029583
PCT Pub. Date: Feb. 27, 2014

(65) Prior Publication Data
US 2015/0313514 A1    Nov. 5, 2015

(30) Foreign Application Priority Data
Aug. 22, 2012  (DE) .................. 10 2012 107 747

(51) Int. Cl.
*A61B 5/15*    (2006.01)
*A61B 5/151*    (2006.01)

(52) U.S. Cl.
CPC ...... *A61B 5/1411* (2013.01); *A61B 5/150022* (2013.01); *A61B 5/15113* (2013.01);
(Continued)

(58) Field of Classification Search
None
See application file for complete search history.

(56) References Cited

U.S. PATENT DOCUMENTS

2002/0120216 A1* 8/2002 Fritz ................... A61B 5/15146
600/583
2003/0083686 A1* 5/2003 Freeman ............ A61B 5/15178
606/181
(Continued)

FOREIGN PATENT DOCUMENTS

DE    10312357    7/2004
EP    1190674    3/2002
(Continued)

OTHER PUBLICATIONS

German Examination Report, dated Jul. 2, 2015, in German patent application serial No. 102012107747.9, 3 pp. (In German language).
(Continued)

*Primary Examiner* — Devin B Henson
*Assistant Examiner* — Benjamin S Melhus
(74) *Attorney, Agent, or Firm* — Leydig, Voit & Mayer, Ltd.

(57) ABSTRACT

The application relates to a lancing device for obtaining samples of body fluid, said device comprising: a base body which is rotationally symmetrical with relation to the longitudinal axis thereof and on one longitudinal end of which a positioning surface with an exit opening is arranged; a lancet cartridge for receiving a plurality of lancets; a drive device for moving a lancet held in the lancet cartridge back and forth along the longitudinal axis; and a transport device for transporting lancets on a plane perpendicular to the longitudinal axis. The exit opening is located substantially centrally in the positioning surface and the lancet cartridge has a guide track for the lancets, in which track said lancets can be positioned in such a way that their tips can emerge from the exit opening during the movement back and forth.

16 Claims, 5 Drawing Sheets

Figure 1:
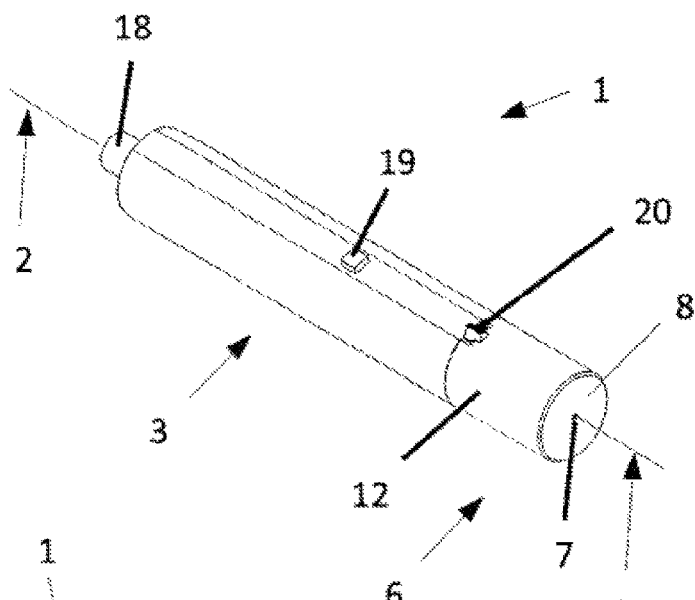

(52) U.S. Cl.
CPC ...... *A61B 5/15115* (2013.01); *A61B 5/15117* (2013.01); *A61B 5/15153* (2013.01); *A61B 5/15163* (2013.01); *A61B 5/15171* (2013.01); *A61B 5/150412* (2013.01); *A61B 5/150503* (2013.01); *A61B 5/1513* (2013.01)

(56) References Cited

U.S. PATENT DOCUMENTS

| | | | | |
|---|---|---|---|---|
| 2005/0115980 | A1* | 6/2005 | Grandy | A61H 39/08 221/66 |
| 2010/0113973 | A1* | 5/2010 | Hibner | A61B 10/0096 600/567 |
| 2010/0168616 | A1* | 7/2010 | Schraga | A61B 5/15146 600/583 |
| 2012/0016315 | A1* | 1/2012 | Radmer | A61M 5/008 604/240 |
| 2012/0041373 | A1* | 2/2012 | Bruehwiler | A61M 5/002 604/173 |
| 2016/0106925 | A1* | 4/2016 | Boesen | A61M 5/008 604/506 |

FOREIGN PATENT DOCUMENTS

| | | |
|---|---|---|
| EP | 2130493 | 12/2009 |
| EP | 2236082 | 11/2011 |
| WO | 2001/00090 | 1/2001 |
| WO | 2008/064333 | 5/2008 |
| WO | 2009/046957 | 4/2009 |

OTHER PUBLICATIONS

Search Report, dated Oct. 7, 2013, corresponding to International Application No. PCT/EP2013/065737 (filed Jul. 25, 2013), parent of the present application, 3 pp.

* cited by examiner

LANCING DEVICE FOR OBTAINING SAMPLES OF BODY FLUID

CROSS-REFERENCE TO RELATED APPLICATIONS

This application is a U.S. National Stage Application filed under 35 U.S.C. § 371 of International Application No. PCT/EP2013/065737, filed Jul. 25, 2013, which claims the benefit of German Application No. 10 2012 107 747.9, filed Aug. 22, 2012. All of these applications are hereby incorporated by reference in their entireties.

The invention relates to a lancing device for obtaining bodily fluid samples according to the preamble of claim 1. The invention further relates to a lancet magazine for a lancing device of this type and to a lancet band for a lancet magazine of this type.

A lancing device of this type is already known from WO 2006/027255 A1. This lancing device has a lancet magazine in the form of a magazine drum in which the lancets, which can be inserted into it, are arranged in a rotationally symmetrical manner about an axis of rotation of the magazine drum and can be moved along a circular path. In this respect, in each case, a lancet is positioned in such a way that the tip of the needle thereof can be moved out of an outlet opening of the lancing device and back into the interior of the lancing device by means of a drive device. The outlet opening is arranged off-centre on the outer edge of a positioning face of the lancing device, in a manner corresponding to the circular path which the lancets follow inside the magazine drum.

When using lancing devices of this type, users of the lancing device, in particular the elderly, often fail to consider that the outlet opening for the needle tip of the lancet is not located centrally on the positioning face of the lancing device, which is formed substantially rotationally symmetrically about the longitudinal direction thereof. Since the users intuitively assume a central needle outlet for lancing devices of this type, this often results in very painful lancing procedures, since the target site actually aimed for by the user is missed and an unintended site is injured.

Generally, a needle outlet opening which is arranged off-centre makes precise determination of the outlet opening by the user difficult, since the user has to make a precise check on the position of the outlet opening prior to each use. Even if the user makes this check each time, targeted positioning of the outlet opening over the desired lancing site is still made more difficult.

However, there is the possibility of an eccentric arrangement of a magazine drum in a lancing device of this type. Nonetheless, this does make a central needle outlet possible. However, for this purpose either the constructional space has to be made correspondingly larger, leading to a more unwieldy lancing device, or else the number of lancets which can be received in a magazine of this type is reduced, in such a way that the lancet magazine has to be refilled more frequently. Both solutions thus result in a reduction in comfort for the user.

Another solution is described in WO 2006/083676 A2. This prior art provides that the lancets are arranged axially rather than radially. This solution is not just of a very complex construction. Rather, a lancing device of this type can only store a relatively small number of lancets, and barely represents an improvement on the lancing devices comprising single lancets in terms of handling.

The object of the invention is therefore to further develop a lancing device in accordance with the preamble of claim 1 in such a way that simple positioning of the outlet opening of the lancing device for the tip of the lancet at the desired lancing site is made possible, and the rest of the handling of the lancing device is also made comfortable for the user.

This object is achieved by a lancing device having the features of claim 1. Advantageous configurations of the invention can be found in the dependent claims.

The lancing device according to the invention for obtaining bodily fluid samples basically shows the following:
a) a base body, which is substantially rotationally symmetrical about the longitudinal axis thereof and which, on one longitudinal-face end thereof, has a positioning face with an outlet opening,
b) a lancet magazine for receiving a plurality of lancets, which is held replaceably in the base body,
c) a drive device for moving a lancet arranged in the lancet magazine back and forth in the direction of the longitudinal axis, said lancet being positioned therein in such a way that the tip thereof can exit the outlet opening during the movement back and forth.
d) a transport device for further transportation of the lancets held in the lancet magazine in a plane perpendicular to the longitudinal axis,
the outlet opening being arranged substantially centrally in the positioning face, and the lancet magazine comprising a guidance path for the lancets, in which the lancets can be positioned in such a way that the tips thereof can exit the outlet opening during the movement back and forth.

For the further discussion, it should be noted in advance that in the following the term "needles" includes not only cylindrical metal, plastics material or ceramic elements or similar elements, but also planar, elongate metal, plastics material or ceramic elements or similar elements, which optionally comprise not only a tip but also at least one cutting edge and which are suitable for penetrating tissue to take samples of bodily fluids, in particular to take blood samples.

Because of the lancing device according to the invention, it is now possible for the outlet opening for the tips of the needles of the lancets to be arranged centrally on the positioning face, the lancets held in the lancet magazine still being displaceably held by the transport device in a plane perpendicular to the longitudinal axis of the base body of the lancing device. Thus, in the lancing device according to the invention, the longitudinal axis of the base body of the lancing device extends through the outlet opening in the positioning face.

The guidance path now no longer describes a circular path about the longitudinal axis of the lancing device. In this case, the guidance path is formed in such a way that the lancets are displaceable therein in a plane perpendicular to the longitudinal axis of the base body of the lancing device by means of the transport device. In this respect, in a plan view, the guidance path may take on completely different planar or two-dimensional geometric shapes. In this respect, the only limitation on the guidance path is that it must comprise a portion through which the longitudinal axis of the base body of the lancing device extends when the lancet magazine is positioned in the lancing device. As a result, the needle of a lancet can be positioned in such a way that when the needle is moved back and forth by the drive device the needle exits the outlet opening of the positioning face and can also be displaced through the outlet opening into the interior of lancing device again.

Simple and comfortable handling is thus made possible for the user of the lancing device according to the invention. When using the lancing device, to position it precisely he/she merely needs to orientate himself/herself towards the longitudinal axis of the base body of the lancing device or towards the centre of the positioning face respectively. If he/she places the positioning face substantially centrally on the desired lancing site, he/she can assume that the tip of the needle of the lancet will encounter the lancing site as desired.

In a first advantageous embodiment of the invention, the base body has a removable cap, which contains the positioning face with the outlet opening. This measure provides that the lancet magazine arranged in the lancing device is protected from external influences, in such a way that no soiling or contamination respectively of the lancets held in the lancet magazine is possible. This also minimises a risk of infection for the user of the lancing device.

The embodiment whereby an outer magazine housing, having an outlet opening corresponding to the outlet opening, is provided for the lancet magazine has the same aim. Further, it may also be provided that an outer magazine housing of this type itself has the positioning face with the outlet opening. In this case, an outlet opening in the removable cap is not necessary. Rather, a cap of this type without an outlet opening would prevent injuries due to incorrect operation, since when a movement back and forth of a needle of a lancet, arranged in the guidance path in the longitudinal axis of the base body, is released, it can exit the outlet opening of the outer magazine housing, but cannot penetrate through a cap when it is put on.

Further, in accordance with a further concept of the invention, an outer magazine housing cover, which further protects the lancet magazine against external influences, is provided for the outer magazine housing. It merely has to be ensured that the drive device can act through this outer magazine housing cover, for which purpose said cover merely has to comprise an opening adapted to the drive device.

The drive device comprises a drive plunger, which can be coupled and decoupled via a release plunger to a needle of the lancet which is positioned in such a way that the tip of the needle thereof can exit the outlet opening when the needle moves back and forth. This measure does not just ensure reliable travel of the tip of the needle of the lancet out of the outlet opening. Rather, the drive plunger also entrains the needle again upon retracting, in such a way that said needle is held in the lancet body thereof in the lancet magazine again.

For the displacement back and forth, the drive device is for example spring-loadable. The base body therefore comprises a tensioning element for tensioning the drive device under a spring load and a trigger element for slackening the drive device. Of course, it is also possible to provide the drive device with a motor, in particular an electric motor. However, spring loading is preferred for this purpose, since it guarantees a short dwell time of the tip of the needle of the lancet in the lancing site and thus minimises the lancing time and thus the potential lancing pain for the user.

In a further advantageous embodiment of the invention, a clock device is provided, which is formed to move the lancet, which is positioned in such a way that the tip thereof can exit the outlet opening during the movement back and forth, out of the position thereof in the guidance path of the lancet magazine and to move a lancet which is adjacent thereto into this position. This ensures that each lancet located in the lancet magazine is only used once. Residues of bodily fluids, in particular blood, generally still adhere to the needle tip of a used lancet which pose a risk of infection for further users of the same lancing device if they are not moved out of the position for the movement back and forth of the needle of the lancet. A potential risk of infection is thus further reduced by this measure. However, to prevent used lancets from rotating continuously in the lancet magazine and possibly also being reused unintentionally by a user, a stop device having a locking function may be provided within the lancet magazine, making it necessary to remove a lancet magazine when each lancet within the lancet magazine has been used once.

The clock device may be formed to be manually operable by means of a clock trigger element. However, it is also possible to form the clock device in such a way that it repositions the lancets automatically, preferably by way of a spring mechanism or an electric motor.

In accordance with a further advantageous concept of the invention, the guidance path of the lancet magazine is formed in such a way that the lancets received therein are subject to restricted guidance. This ensures that the lancets within the lancet magazine can only carry out desired movements, further simplifying the handling of the lancing device and increasing the operating comfort for the user.

In this case, the guidance path of the lancet magazine is advantageously formed either to receive an open or closed lancet band, in which lancet bodies of the lancets are interconnected via at least one connection band or via connection webs respectively, or to receive individual lancets. If a lancet band is used in the lancet magazine, it is only possible to replace the entire lancet band. If individual lancets are used, these may of course also be replaced individually. However, this again increases the risk that previously used lancets may remain in the lancet magazine and be used a second time, even if this is not intended by the user, increasing a potential risk of infection. Therefore, the use of lancet bands is preferred. In particular, lancet bands of this type have to be formed flexibly as a result of the guidance path of the lancet magazine. However, this flexibility can be achieved in a simple manner by way of the aforementioned connection bands or connection webs respectively.

The invention also independently protects a lancet magazine, as disclosed in greater detail previously above, for use in an above-disclosed lancing device.

Further, a lancet band, as disclosed in greater detail previously above, for the above-disclosed lancet magazine is also independently protected.

Here, a stop element, which prevents the lancet band from being conveyed onwards in the lancet magazine once all of the lancets of the lancet band have been moved back and forth once and each lancet has thus been used once, may be provided on a lancet band end.

This stop element thus cooperates with or engages in a stop element of the lancet magazine respectively so as to achieve the above-disclosed locking function for the conveyance of lancets onwards within the conveyance path of the lancet magazine.

Further aims, advantages, features and possible applications of the present invention can be seen in the following description of embodiments with reference to the drawings. In this context, all of the features which are described and/or shown in the drawings, in isolation or in any reasonable combination, form the subject matter of the present invention, irrespective of how they are compiled in the claims or the dependencies thereof.

Figure 2:
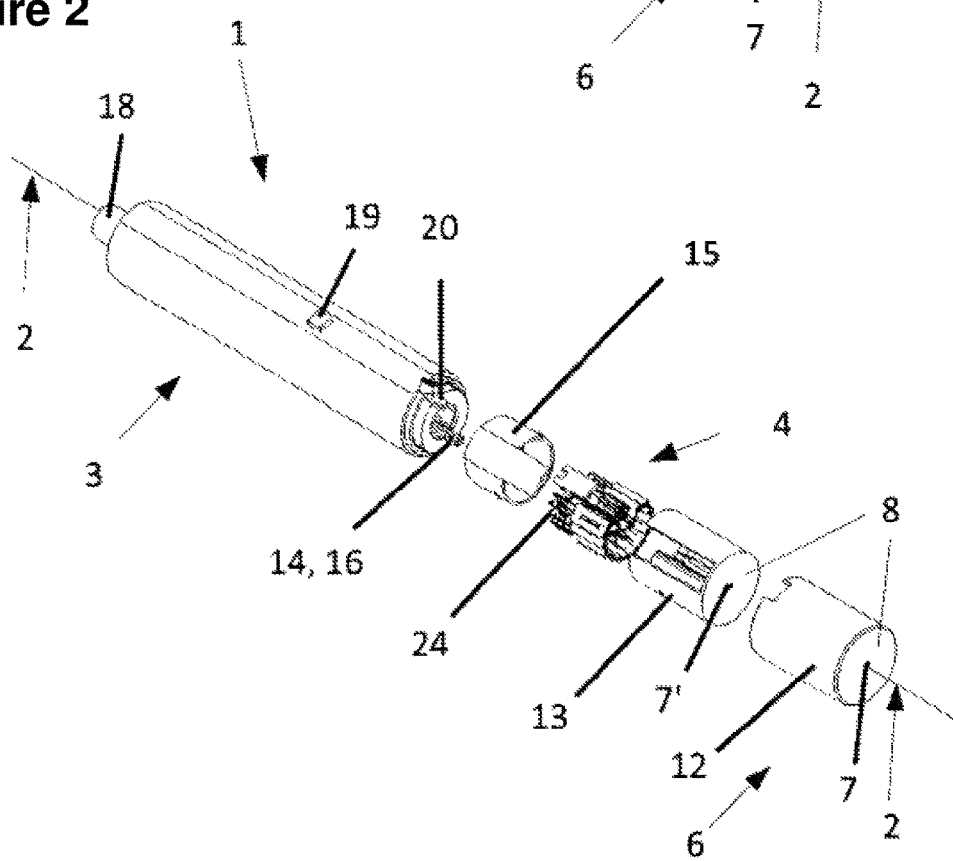
Figure 3:
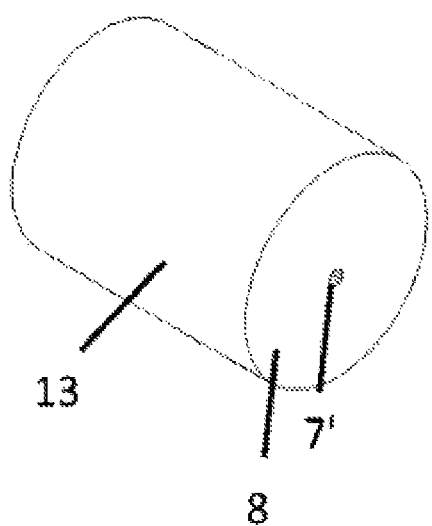
Figure 4:
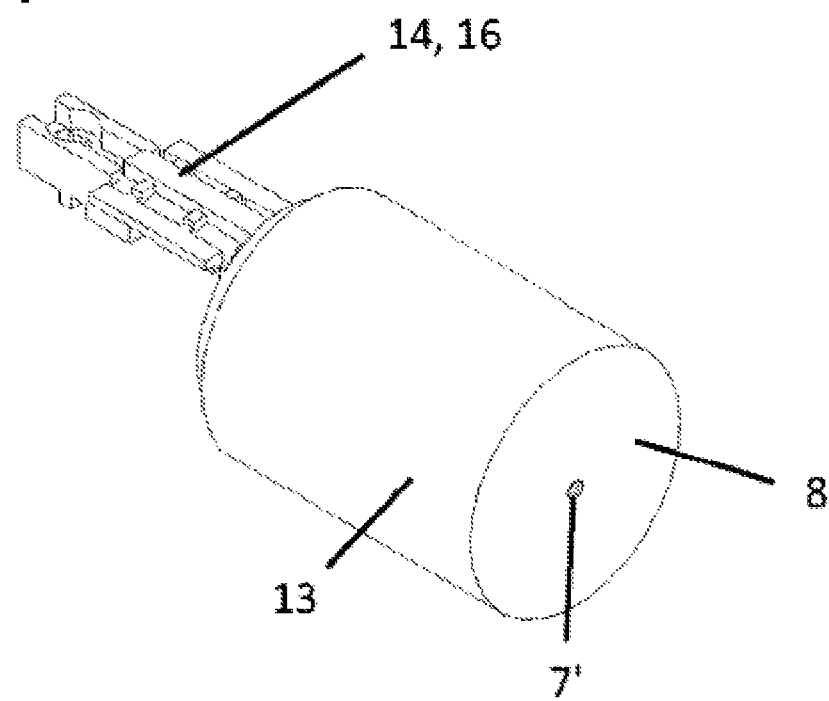
Figure 5:
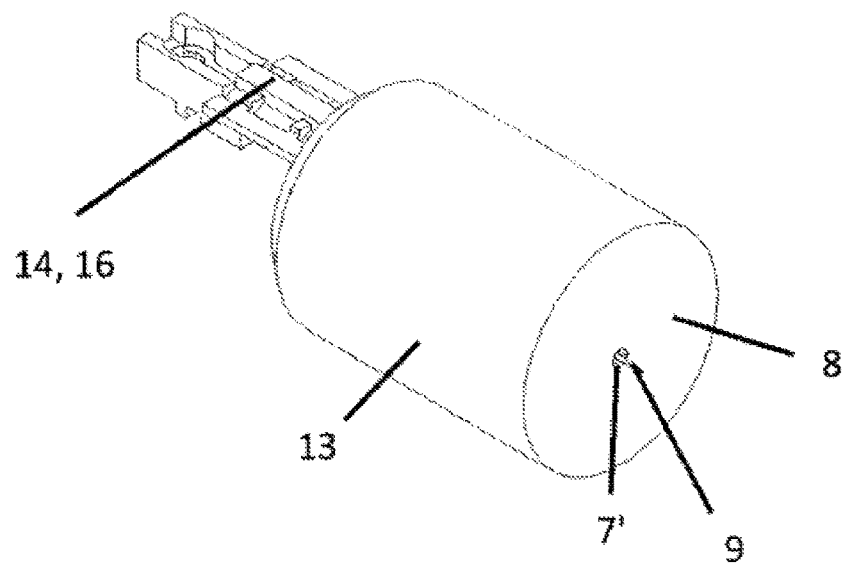
Figure 6:
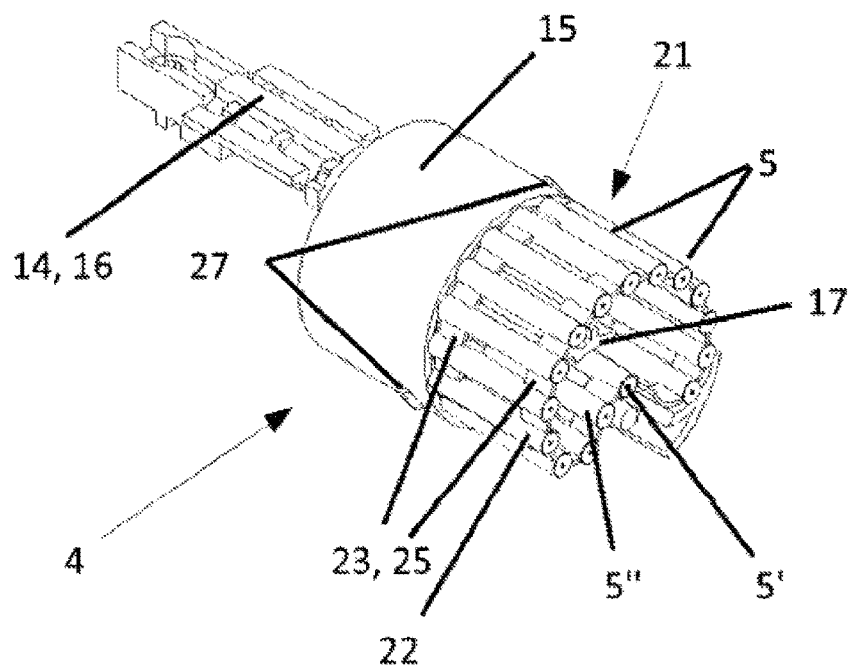
Figure 7:
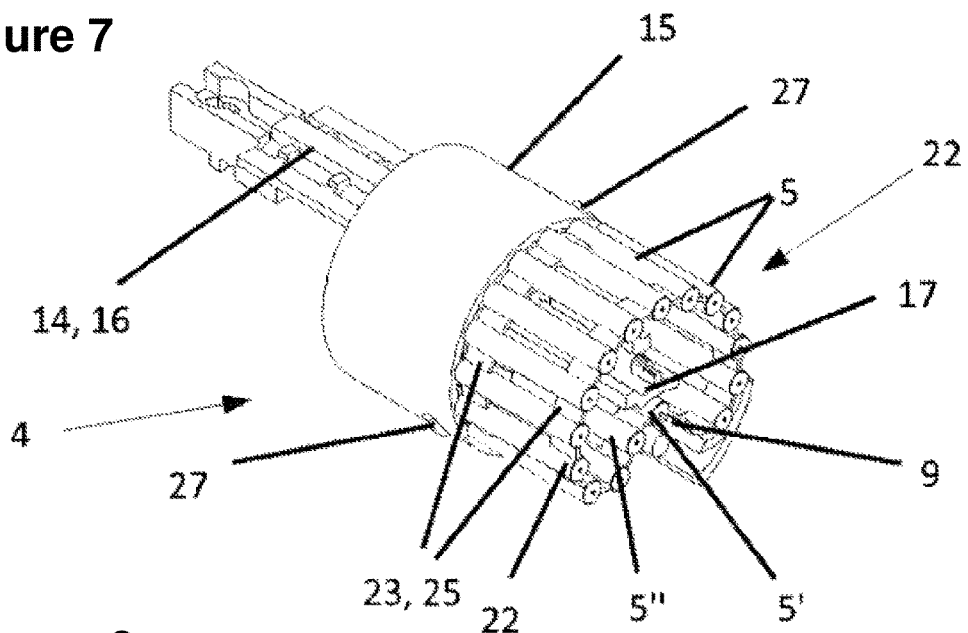
Figure 8:
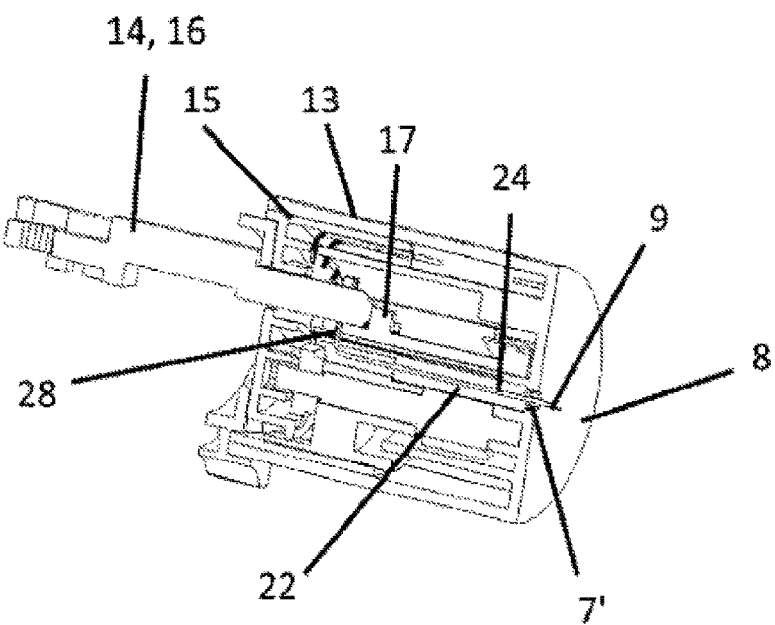
Figure 9:
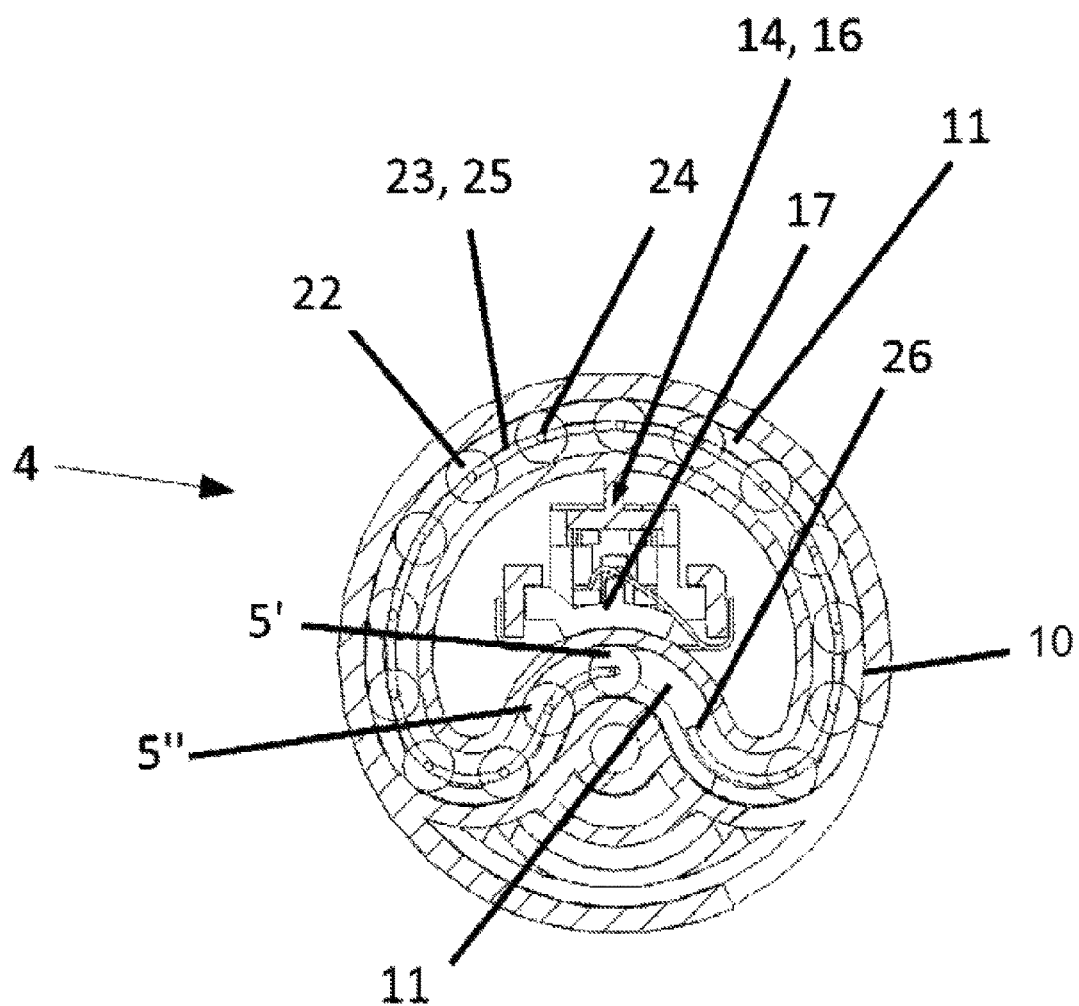

In the drawings:

FIG. 1 is a perspective view of an embodiment of a lancing device according to the invention when closed, FIG. 2 is an exploded view of the lancing device of FIG. 1, FIG. 3 is a perspective view of an outer magazine housing of the lancing device according to the FIGS. 1 and 2, FIG. 4 shows the outer magazine housing of FIG. 3 with a lancet magazine inserted therein, in which a drive plunger of a drive unit engages, FIG. 5 shows the outer magazine housing of FIG. 4 having a tip of a needle of a lancet exiting an outlet opening of the outer magazine housing, FIG. 6 is a perspective view of an embodiment of a lancet magazine in which a drive plunger of a drive unit engages, FIG. 7 shows the lancet magazine of FIG. 6, the needle of a lancet being displaced in the lancet body thereof, FIG. 8 is a cross-section of the lancet magazine of FIG. 6 along a longitudinal axis, FIG. 9 is a cross-section of the lancet magazine of FIG. 6 perpendicular to a longitudinal axis.

FIG. 1 shows an embodiment of a lancing device 1 according to the invention. This lancing device 1 is formed substantially rotationally symmetrically about a longitudinal axis 2 of a base body 3 of the lancing device 1. On one end 6, the base body has a cap 12, by means of which a lancet magazine 4, arranged in the interior of the lancing device 1 or of the base body 3 respectively, can be covered.

The lancing device 1 is provided with a drive device 14 (not shown in greater detail in the drawings), by means of which a needle 24 of a lancet 5 located in the lancet magazine 4 can be moved out through the outlet opening 7 and also moved back into the lancing device 1, by spring loading.

For the drive device 14 to be able to move a needle 24 back and forth, a trigger element 19, by means of which a one-time movement back and forth of the needle 24 can be triggered, is provided on the base body 3 of the lancing device 1. However, a movement back and forth of this type of the needle 24 can only be initiated if the spring-loading of the drive device 14 has previously taken place. For this purpose, a tensioning element 18 is provided on the end of the lancing device 1 or base body 3 opposite the end 6, the drive device being loaded with a spring force when said tensioning element is actuated.

Further, a further clock trigger element 20 for a clock device (not shown in greater detail in the drawings) is arranged on the base body 3. This clock trigger element 20 serves to initiate a movement of a lancet 5', which has been used once, within the guidance path 11 of the lancet magazine 4 after the needle 24 of the lancet 5' has been moved by means of the drive device 14 in such a way that the tip 9 of the needle 24 has exited through the outlet opening 7 and subsequently the needle 24 has been pulled back again completely into the lancing device 1. The movement initiated by the clock trigger element 20 takes place in such a way that the lancet 5' in the guidance path 11 is conveyed out of the original position thereof in the lancet magazine 4 and an adjacent lancet 5" is moved into this position, in such a way that this lancet 5" can now be displaced back and forth by the drive device 14.

FIG. 2 is an exploded view of the lancing device 1 of FIG. 1, such that the parts in the interior of the lancing device can also be seen. The drive plunger 16 of a drive device 14, which is in an operative connection with the trigger element 19 and the tensioning element 18, projects out of the base body 3 of the lancing device 1, on which the tensioning element 18, as well as the trigger element 19 and the clock trigger element 20 are arranged. When the lancing device 1 is closed, this drive plunger 16 is in an operative connection with a release plunger 17 for a needle 24 of a lancet 5', which is positioned in the lancet magazine 4 in such a way that the tip 9 thereof can exit through the outlet opening 7, 7' on the positioning face 8. As is shown in particular in FIG. 2, both an outer magazine housing 13 and an outer magazine housing cover 15 are provided for the lancet magazine 4. The lancet magazine 4 can be received so as to be substantially encapsulated therein, in such a way that the lancets 5, 5' and 5" located in the lancet magazine 4 are substantially protected from external influences and thus from soiling and contamination, even when the cap 12 is not applied to the lancing device 1.

FIG. 3 shows the substantially cylindrical outer magazine housing 13 with the positioning face 8 and an outlet opening 7' located therein for a needle 24, the lancet magazine 4 being received therein.

FIG. 4 additionally shows how the drive plunger 16 of the drive device 14 engages in the lancet magazine 4. In FIG. 4, the drive device 14 is not currently in operation.

In contrast, FIG. 5 shows the operation of the drive device 14, the needle 24 being located in a lancing position in which the tip 9 thereof projects out of the opening 7' in the positioning face 8 of the outer magazine housing 13.

FIG. 6 shows the lancet magazine 4 of FIG. 4 again, but without the outer magazine housing 13. This drawing clearly shows a lancet band 21 inserted into the lancet magazine 4 and how it is guided through the lancet magazine 4. The guidance path 11 for the lancets 5, 5', 5" or for the lancet band 21 respectively describes the shape of a kidney. However, this is merely one possible embodiment. A plurality of guidance paths not shown in the drawings are also possible.

The retracted release plunger 17 is also clearly visible in FIG. 6, in such a way that the tip 9 of the needle 24 of the lancet 5' has not exited the lancet body 22 thereof. FIG. 6 further shows two snap-in hooks 27 on the outer magazine housing cover 15, in which the lancet magazine 4 is held. By means of these snap-in hooks 27, the outer magazine housing 13 can be fixed to the outer magazine housing cover 15.

FIG. 7 shows the lancet magazine 4 of FIG. 5 but without an outer magazine housing 13. The advanced release plunger 17 can be seen clearly here, in such a way that the tip 9 of the needle 24 of the lancet 5' has exited the lancet body 22 thereof.

FIG. 8 is in turn a cross-section of FIG. 7, but having the outer magazine housing 13 fixed to the outer magazine housing cover 15. The engagement of drive plunger 16 of the drive device 14 and the release plunger in a curved needle end 28 of the needle 24 is also shown. In this respect, the needle 24 is displaced in the lancet body 22 thereof in such a way that the tip 9 thereof has exited the outlet opening 7' in the positioning face 8 of the outer magazine housing 13. The tip 9 is thus located in the lancing position thereof. However, this is merely a snapshot, since the needle 24 does not dwell in this position. Rather, the forward movement, the final position of which is shown in FIGS. 7 and 8, is immediately followed by a retraction of the needle 24, until the tip is received in the lancet body 22 again. However, the lancet body 22 does not merely serve to guide the needle 24 during the movement back and forth thereof. Rather, the lancet body 22 fixes the lancet 5' in the lancet magazine, making it possible for the first time for the needle 24 to move back and forth in the lancet body 22, and thus for the tip 9 of the needle 24 to exit the outlet opening 7, 7' of the positioning face.

Finally, FIG. 9 is a cross-section of the lancet magazine 4 of FIG. 6 perpendicular to the longitudinal axis 2. The special configuration of the guidance path 11 for the lancet band 22 can be seen in this drawing in particular. As a result, it is possible to position a lancet 5' of the lancet band 22 in such a way that the tip 9 of the needle 24 of the lancet 5' exits the outlet opening 7, 7', arranged centrally in the positioning face 8, and can take on its lancing position. The restricted guidance of the lancets 5, 5', 5" within the guidance path 11 can also be seen clearly in this drawing, as can the engagement of the drive plunger 16 of the drive device 14 and the release plunger 17 in the lancet magazine.

LIST OF REFERENCE NUMERALS

1 Lancing device
2 Longitudinal axis
3 Base body
4 Lancet magazine
5 Lancet
5' Lancet
5" Lancet
6 Longitudinal-face end
7 Outlet opening
7' Outlet opening
8 Positioning face
9 Tip
10 Transport device
11 Guidance path
12 Cap
13 Outer magazine housing
14 Drive device
15 Outer magazine housing cover
16 Drive plunger
17 Release plunger
18 Tensioning element
19 Trigger element
20 Clock trigger element
21 Lancet band
22 Lancet body
23 Connection band
24 Needle
25 Connecting webs
26 Lancet band end
27 Snap-in hooks
28 Needle end

The invention claimed is:

1. A lancing device for obtaining bodily fluid samples comprising:
   a) a base body, which is rotationally symmetrical about a longitudinal axis thereof which, on one longitudinal face end thereof has a positioning face with an outlet opening,
   b) a lancet magazine for receiving a plurality of lancets, which is held replaceably in the base body,
   c) a drive device for moving a lancet arranged in the lancet magazine back and forth in the direction of the longitudinal axis, said lancet being positioned therein in such a way that a tip thereof exits the outlet opening during the back and forth movement,
   d) a transport device for further transportation of the lancets held in the lancet magazine,
   e) the outlet opening being arranged centrally in the positioning face so as to be co-axial with the longitudinal axis,
   f) the lancet magazine having a guidance path for the lancets, such that the lancet to be moved back and forth in the longitudinal direction by the drive device is transported to a center position of the device, wherein the central position is co-axial with the longitudinal axis and the outlet opening,
   wherein the drive device is able to contact the lancet to be moved back and forth at this central position and move the lancet to be moved back and forth through the base body so that the lancet tip exits the outlet opening during the back and forth movement, wherein
   g) lancets in the transport device for further transportation of the lancets held in the lancet magazine are displaceably held in a plane which is perpendicular to the longitudinal axis,
   h) the guidance path is formed in a non-circular path about the longitudinal axis of the lancing device,
   i) in each case, the drive device for moving the lancet arranged in the lancet magazine back and forth in the direction of the longitudinal axis merely moves one of the lancets in the lancet magazine back and forth in the direction of the longitudinal axis wherein the lancet is guided in a lancet body, and,
   j) the guidance path of the lancet magazine is formed to receive an open or closed lancet band;
   wherein the guidance path is non-linear within a plane perpendicular to the longitudinal axis, or non-linear within a plane parallel to the plane perpendicular to the longitudinal axis.

2. The lancing device according to claim 1, wherein the base body has a removable cap which contains the positioning face with the outlet opening.

3. The lancing device according to claim 1, wherein an outer magazine housing, having a further outlet opening corresponding to the outlet opening, is provided for the lancet magazine.

4. The lancing device according to claim 3, wherein an outer magazine housing cover is provided for the outer magazine housing.

5. The lancing device according to claim 1, wherein the drive device comprises a drive plunger, which can be coupled and decoupled via a release plunger to a needle of the lancet which is positioned in such a way that the tip of the needle can exit the outlet opening during the back and forth.

6. The lancing device according to claim 1, wherein the base body has a tensioning element for tensioning the drive device under a spring load and a trigger element for slackening the drive device.

7. The lancing device according to claim 1, wherein a clock device is provided, which is formed to move the lancet, which is positioned in such a way that the tip thereof can exit the outlet opening during the back and forth movement, out of the position thereof in the guidance path of the lancet magazine and to move an adjacent lancet into this position.

8. The lancing device according to claim 7, wherein the clock device is formed to be manually operable by means of a clock trigger element.

9. The lancing device according to claim 7, wherein the clock device is formed in such a way that it repositions the lancets automatically by way of a spring mechanism or an electric motor.

10. The lancing device according to claim 1, wherein the guidance path of the lancet magazine provides restricted guidance to the lancets received in the lancet magazine.

11. The lancing device according to claim 1, wherein the guidance path of the lancet magazine is formed to receive individual lancets.

12. The lancing device according to claim 1, further comprising the lancet band.

13. The lancet device according to claim 12, wherein a stop element, which prevents the lancet band from being conveyed onwards in the lancet magazine once all of the lancets of the lancet band have been moved back and forth once, is provided on a lancet band end.

14. The lancet device according to claim 13, wherein the stop element cooperates with or engages in a stop element of the lancet magazine.

15. A lancing device for obtaining bodily fluid samples comprising:
   a) a base body, which is rotationally symmetrical about a longitudinal axis thereof which, on one longitudinal face end thereof has a positioning face with an outlet opening,
   b) a lancet magazine for receiving a plurality of lancets, which is held replaceably in the base body,
   c) a drive device for moving a lancet arranged in the lancet magazine back and forth in the direction of the longitudinal axis, said lancet being positioned therein in such a way that a tip thereof exits the outlet opening during the back and forth movement,
   d) a transport device for further transportation of the lancets held in the lancet magazine,
   e) the outlet opening being arranged centrally in the positioning face so as to be co-axial with the longitudinal axis,
   f) the lancet magazine having a guidance path for the lancets, such that the lancet to be moved back and forth in the longitudinal direction by the drive device is transported to a center position of the device wherein the central position is co-axial with the longitudinal axis and the outlet opening,
   wherein the drive device is able to contact the lancet to be moved back and forth at this central position and move the lancet to be moved back and forth through the base body so that the lancet tip exits the outlet opening during the back and forth movement, wherein
   g) lancets in the transport device for further transportation of the lancets held in the lancet magazine are displaceably held in a plane which is perpendicular to the longitudinal axis,
   h) the guidance path is formed in a non-circular path about the longitudinal axis of the lancing device such that the lancet to be moved back and forth in the longitudinal direction by the drive device is transported from an outer edge of the lancing device to the center position of the device so as to be aligned with the centrally positioned outlet opening,
   i) in each case, the drive device for moving the lancet arranged in the lancet magazine back and forth in the direction of the longitudinal axis merely moves one of the lancets in the lancet magazine back and forth in the direction of the longitudinal axis wherein the lancet is guided in a lancet body, and
   j) the guidance path of the lancet magazine is formed to receive an open or closed lancet band;
   wherein the guidance path is non-linear within a plane perpendicular to the longitudinal axis, or non-linear within a plane parallel to the plane perpendicular to the longitudinal axis.

16. The lancing device according to claim 1, further comprising one or more connection bands or connection webs attached to each lancet body of the lancets, thereby interconnecting the lancets.

* * * * *